US010488425B2

(12) United States Patent
Ørning et al.

(10) Patent No.: US 10,488,425 B2
(45) Date of Patent: Nov. 26, 2019

(54) CUTTER FOR AN ASSAY CARTRIDGE

(71) Applicant: AXIS-SHIELD AS, Oslo (NO)

(72) Inventors: Lars Ørning, Oslo (NO); Frank Frantzen, Oslo (NO); Andrew Thomas Campbell, Oslo (NO); Arve Strømsheim, Oslo (NO)

(73) Assignee: AXIS-SHIELD AS, Oslo (NO)

( * ) Notice: Subject to any disclaimer, the term of this patent is extended or adjusted under 35 U.S.C. 154(b) by 0 days.

(21) Appl. No.: 15/817,242

(22) Filed: Nov. 19, 2017

(65) Prior Publication Data

US 2018/0156830 A1 Jun. 7, 2018

Related U.S. Application Data

(62) Division of application No. 14/357,562, filed as application No. PCT/GB2012/052793 on Nov. 9, 2012, now Pat. No. 9,857,384.

(30) Foreign Application Priority Data

Nov. 11, 2011 (GB) .................................... 1119521.1

(51) Int. Cl.
*B01L 3/00* (2006.01)
*B01L 3/02* (2006.01)
(Continued)

(52) U.S. Cl.
CPC ................ *G01N 33/92* (2013.01); *B01L 3/02* (2013.01); *B01L 3/0275* (2013.01); *B01L 3/50* (2013.01);
(Continued)

(58) Field of Classification Search
CPC ........ G01N 33/48; G01N 33/92; G01N 35/10; G01N 21/03; B01L 3/50855; B01L 3/02;
(Continued)

(56) References Cited

U.S. PATENT DOCUMENTS 5,460,782 A 10/1995 Coleman
7,632,462 B2 12/2009 Holtlund
(Continued)

FOREIGN PATENT DOCUMENTS

CA 2215561 A1 3/1998
EP 1561978 A1 8/2005
(Continued)

OTHER PUBLICATIONS

Communication pursuant to Article 94(3) EPC dated Oct. 11, 2016, issued in EP Application No. 12 787 843.7.
(Continued)

*Primary Examiner* — Maureen Wallenhorst
(74) *Attorney, Agent, or Firm* — Casimir Jones S.C.; Thomas Isenbarger

(57) ABSTRACT

An assay cartridge has a base member (26) that defines at least two wells (30, 32, 34, 36, 38), a pipette (108, 110) positionable in at least one of the wells and a cap member (86) arranged to carry the pipette. The cap member can be releasably fastened to the base member. An extension member (28) defines at least one further well (40, 42, 44) and can be fastened to the base member such that the pipette is then positionable in at least one of the wells of the base and in the further well of the extension member.

9 Claims, 12 Drawing Sheets

Figure 1:
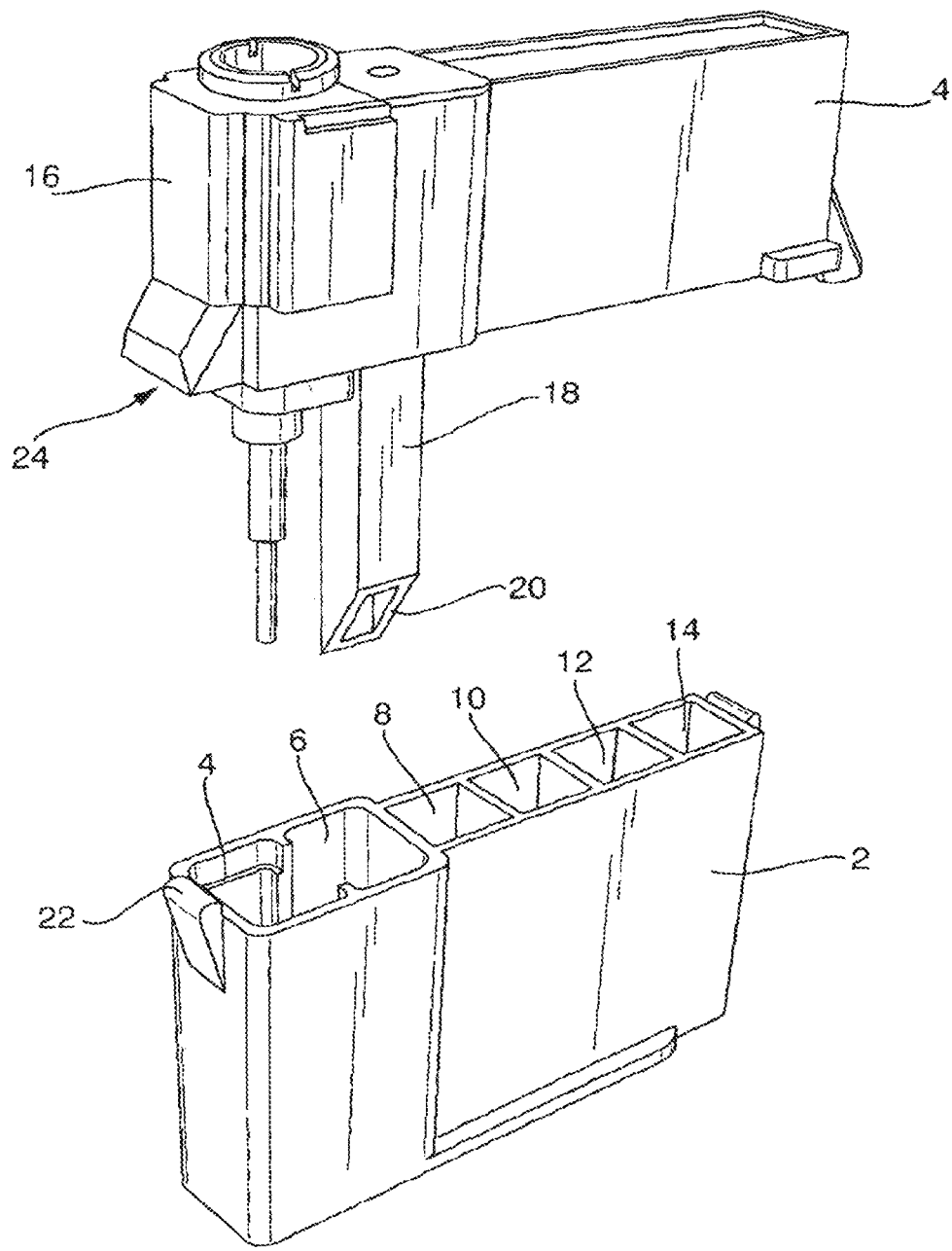

(51) Int. Cl.
*G01N 33/92* (2006.01)
*G01N 33/48* (2006.01)
*G01N 35/10* (2006.01)
*G01N 21/03* (2006.01)
*G01N 21/11* (2006.01)
*F16J 15/02* (2006.01)

(52) U.S. Cl.
CPC .......... *B01L 3/502* (2013.01); *B01L 3/50853* (2013.01); *B01L 3/50855* (2013.01); *F16J 15/02* (2013.01); *G01N 35/10* (2013.01); *B01L 3/022* (2013.01); *G01N 21/03* (2013.01); *G01N 33/48* (2013.01); *Y10T 29/49826* (2015.01); *Y10T 83/929* (2015.04); *Y10T 436/2575* (2015.01)

(58) Field of Classification Search
CPC .......... B01L 3/0275; B01L 3/50; B01L 3/502; B01L 3/50853; B01L 3/022; Y10T 436/11; Y10T 436/25; Y10T 436/2575; Y10T 29/49826; Y10T 83/929
USPC .......... 436/43, 63, 71, 164, 165, 174, 180; 422/401, 402, 403, 407, 68.1, 82.09, 500, 422/501, 512, 520, 547, 552, 554, 559, 422/569, 570; 435/288.3, 288.4, 288.7; 83/651
See application file for complete search history.

(56) References Cited

U.S. PATENT DOCUMENTS

| | | | |
|---|---|---|---|
| 7,943,100 B2 | 5/2011 | Rousseau | |
| 8,728,800 B2 | 5/2014 | Frantzen et al. | |
| 8,997,800 B2 | 4/2015 | Voit et al. | |
| 9,857,384 B2 * | 1/2018 | Orning | B01L 3/02 |
| 2004/0161368 A1 | 8/2004 | Holtlund | |
| 2005/0023772 A1 | 2/2005 | England | |
| 2007/0137645 A1* | 6/2007 | Eason | A61M 15/0028 128/203.15 |
| 2008/0261210 A1 | 10/2008 | Frantzen et al. | |
| 2009/0105679 A1 | 4/2009 | Joubert et al. | |
| 2009/0129987 A1 | 5/2009 | Tanimoto et al. | |
| 2010/0247385 A1 | 9/2010 | Rousseau | |
| 2011/0162755 A1 | 7/2011 | Voit et al. | |
| 2014/0302611 A1 | 10/2014 | Ørning et al. | |
| 2018/0156830 A1 | 6/2018 | Ørning et al. | |

FOREIGN PATENT DOCUMENTS

| | | |
|---|---|---|
| EP | 1906186 A2 | 4/2008 |
| EP | 2194385 | 6/2010 |
| EP | 2776809 B1 | 5/2018 |
| JP | 2004-531725 | 10/2004 |
| WO | 9204978 A1 | 4/1992 |
| WO | 99/61919 A2 | 12/1999 |
| WO | 0158987 A2 | 12/2001 |
| WO | 02090995 A2 | 11/2002 |
| WO | 2005037353 A1 | 4/2005 |
| WO | 2006123660 | 11/2006 |
| WO | 2013068760 A2 | 5/2013 |

OTHER PUBLICATIONS

Japanese Notice of Reasons for Rejection dated May 31, 2016, issued in JP Patent Application No. 2014-540553.
International Search Report of PCT/GB2012/052793, dated May 29, 2013 (May 29, 2013); the whole document.
Extended European Search Report in EP Application No. 18161835.6 dated Apr. 16, 2018.

* cited by examiner

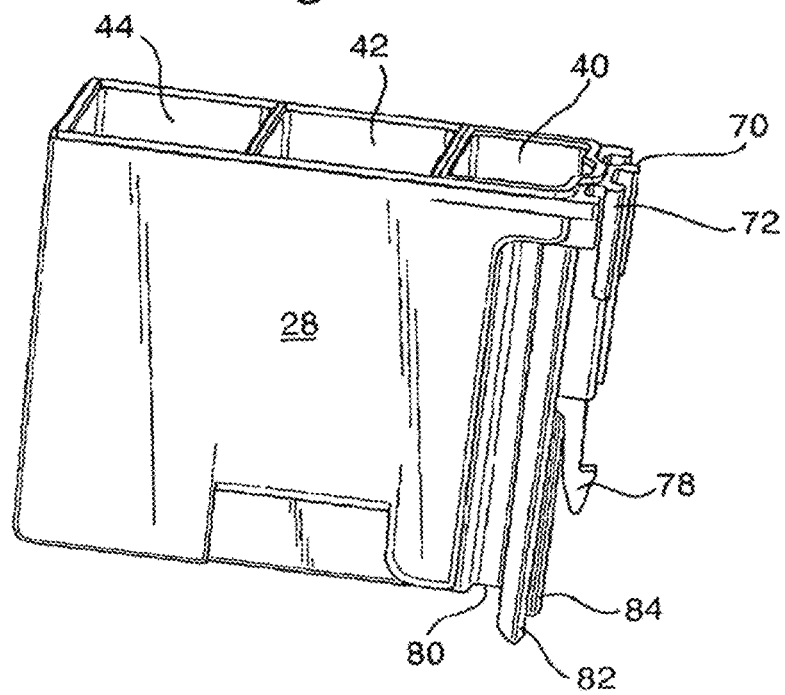
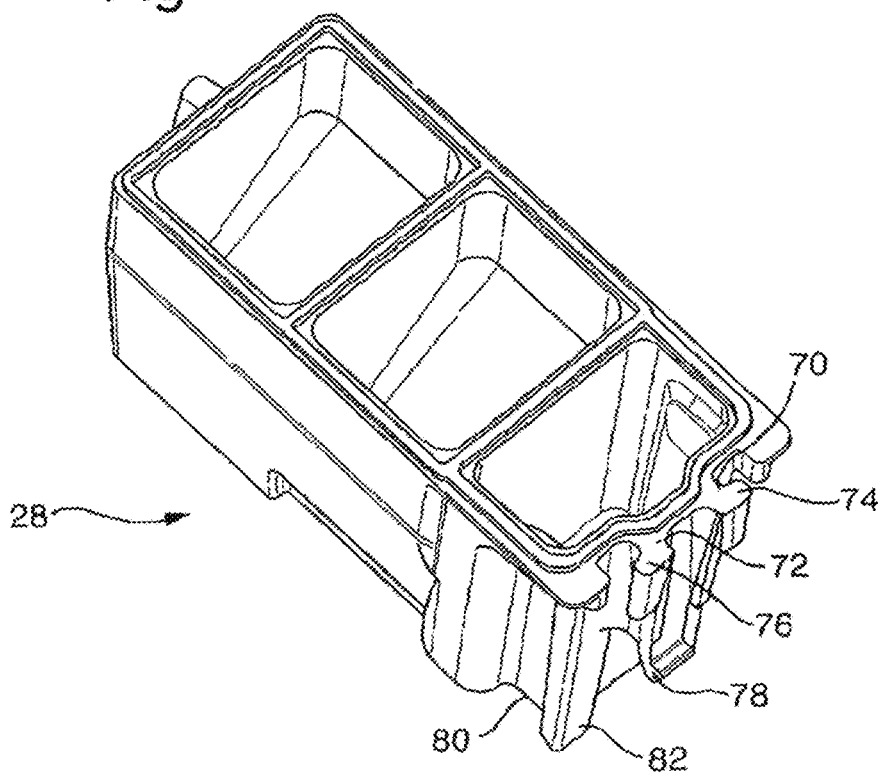

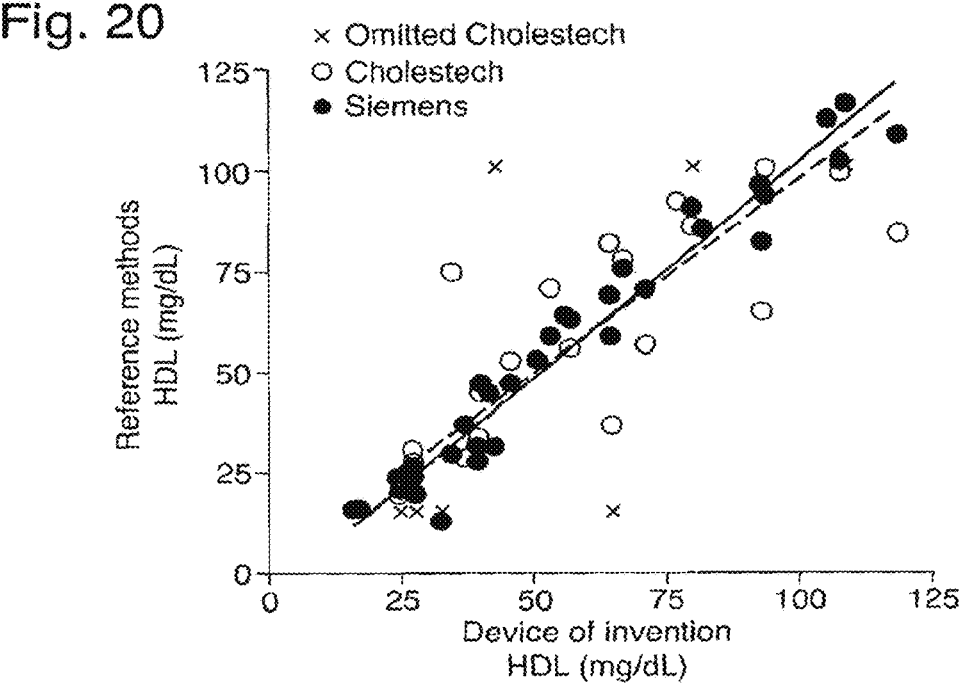

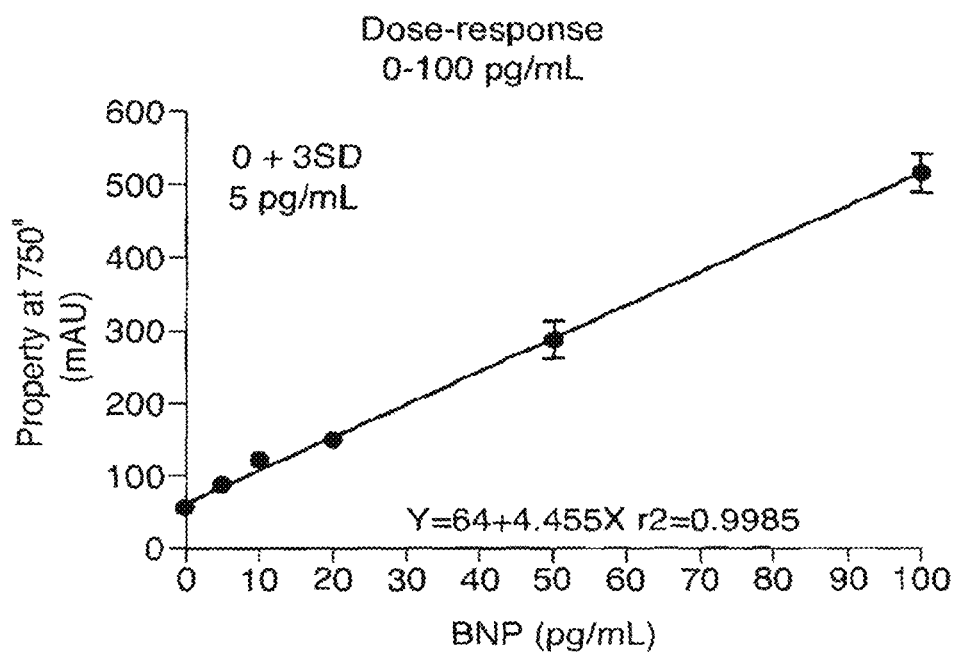
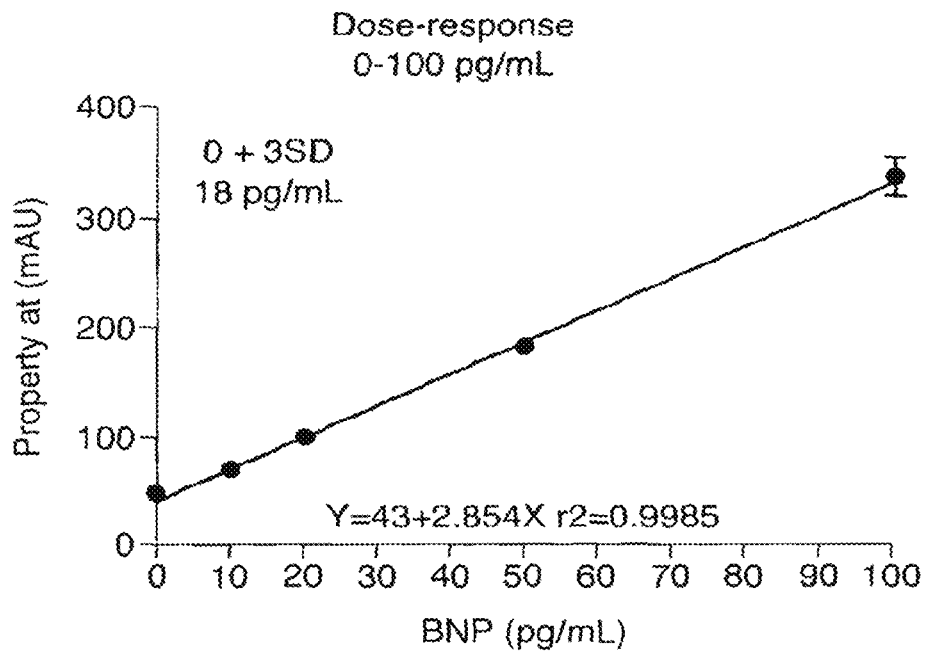

CUTTER FOR AN ASSAY CARTRIDGE

CLAIM PRIORITY

This application is a Divisional of U.S. application Ser. No. 14/357,562, filed on May 9, 2014, now U.S. Pat. No. 9,857,384, which claims the benefit under 35 USC 371 to International Application No. PCT/GB2012/052793, filed Nov. 9, 2012, which claims priority to British Patent Application No. 111952.1, filed on Nov. 11, 2011, each of which is incorporated by reference in its entirety.

This invention relates to assay cartridges and elements thereof, especially assay cartridges usable at the point-of-care, e.g. at the physician's place of work or at the patient's bedside.

A known assay system, devised by the applicant, is described in WO 02/090995. A sample, e.g. of blood, is placed in a disposable assay cartridge. The cartridge comprises at least two wells and a pipette positionable in at least two of said wells. The cartridge is loaded into an assay device, or analyser device, which uses the pipette and the wells of the cartridge to perform a diagnostic assay on the sample. The device may have a light detector for detecting radiation from the cartridge. The cartridge itself can be supplied to the customer (e.g. a physician) pre-filled with the reagents required for a particular assay. The same analyser device can be used to perform a variety of different assays, by loading it with the appropriate cartridge. Examples of assays which can be conducted include measuring the proportion of glycated haemoglobin in blood, and measuring albumin in urine.

The system has been successfully commercialised as the Afinion™ Point-of-Care Analyzer system from Axis-Shield™. The Afinion™ AS100 Analyzer is a commercially available analyser device into which compatible assay cartridges can be loaded.

FIG. 1 shows a prior art assay cartridge. It has a base member 2 and a cap member 4. The base member 2 defines six wells 4-14, four of which 8-14 can contain reagents and are initially sealed by a foil lid (not shown). The cap member 4 carries a detachable capillary-tipped pipette 16 and a pipette 18 with a sloping opening 20 which can be covered by a membrane (not shown). The base member 2 has flexible protrusions 22 which engage with corresponding sockets or holes 24 in the cap member 4 in order to attach the cap member 4 releasably to the base member 2. The cap 4 contains three cutters (not shown) which can pierce the foil lid sealing the four wells 8-14 by urging the cap 4 further onto the base 2.

However the applicant has come to realise that there are certain desirable assays which cannot easily be performed using such a cartridge.

Thus, from a first aspect, the invention provides an assay cartridge comprising:
 a base member that defines at least two wells;
 a pipette positionable in at least one of said wells;
 a cap member arranged to carry the pipette;
 means for releasably fastening the cap member to the base member;
 an extension member that defines at least one further well; and
 means for fastening the extension member to the base member such that, when the extension member is fastened to the base member, the pipette is positionable in at least one of the wells of the base member and is further positionable in the further well of the extension member.

From a further aspect, the invention provides a kit of parts for an assay cartridge, the kit comprising:
 a base member that defines at least two wells;
 a pipette positionable in at least one of said wells;
 a cap member arranged to carry the pipette; and
 an extension member that defines at least one further well, wherein one or both of the base member and the cap member comprises means for releasably fastening the cap member to the base member, and wherein one or both of the base member and the extension member comprises means for fastening the extension member to the base member such that, when the extension member is fastened to the base member, the pipette is positionable in at least one of the wells of the base member and is further positionable in the further well of the extension member.

From a still further aspect, the invention provides a method of manufacturing an assay cartridge, comprising:
 fastening an extension member to a base member, wherein the base member defines at least two wells and the extension member defines at least one further well, such that a pipette is positionable in at least one of the wells of the base member and is further positionable in the further well of the extension member; and
 releasably fastening a cap member to the base member, wherein the cap member carries the pipette.

It will be seen by those skilled in the art that such an assay cartridge has wells defined by, or formed in, two different members. This provides advantages and new possibilities not available with an assay cartridge which has wells defined in only one member.

The extension member may, for example, be formed substantially of a different material from the base member.

In one set of embodiments, for example, the extension member may be formed substantially of a relatively opaque or radiation-impenetrable material, while the base member may be formed substantially of a relatively transparent or radiation-penetrable material. Such an arrangement advantageously allows a light-sensitive reagent to be stored or carried in the cartridge, while still also allowing radiation readings to occur through the (relatively transparent) wall of a well in the base member of the cartridge.

In another set of embodiments, the kit of parts may comprise means to keep the extension member out of contact with the base member while the kit is in storage. For example, the extension member may be substantially enclosed by packaging, such as an air-tight bag. The base member may be packaged similarly, preferably separately from the extension member. This allows reagents contained in the extension member to be stored in different conditions, or in a different atmosphere, from reagents in the base member. For example, one or more wells of the extension member may contain reagents which must be protected from humidity or moisture above a predetermined level (e.g. freeze-dried calibrators or controls), while one or more wells in the base member may contain a liquid reagent, or vice versa. By storing such an extension member in a different atmosphere from the base member, and out of contact with the base member, the transmission of moisture from the liquid reagent to the moisture-sensitive reagent is prevented both via evaporation into the atmosphere and via diffusion directly through the materials of the members (e.g. plastics). This enables assays involving liquid and moisture-sensitive reagents which would not have been possible using a known assay cartridge.

Further surprising advantages can be appreciated when considering the manufacturing of the assay cartridges. The applicant has realised that it is easier to manufacture in plastics, for example, a short cartridge that is homogenous than a longer cartridge. Put another way, for a given manufacturing process, a base member and an extension member will typically each be of more homogenous construction (e.g. in wall thickness or chemical composition) than a single member having similar overall dimensions to the combination of the base member and the extension member. Heterogeneity in the material of the assay cartridge may introduce structural weaknesses which could lead to failure (e.g. cracking) of the cartridge when it is manipulated by an analyser device. Consistent optical properties (e.g. uniform light transmission) in at least a part of the base member can be important when radiation is to be detected from one of the wells through a wall of the base member. An assay cartridge embodying the invention, which has wells in two members, may therefore perform better than a known assay cartridge which has the same number of wells in a single member.

The applicant has also realised that it can be more versatile and economical to manufacture relatively short extension members, e.g. having three wells, which can be combined with base members, e.g. having five wells, as needed, than it is to manufacture larger base members, e.g. having eight wells. The extension member may be fastened to the base member in a production line, or it may be fastened only at the point of care, e.g. in a physician's office or a hospital laboratory. For example, a base member having five-wells for performing an enzymatic reaction on blood could optionally be enhanced by an extension member comprising a filter unit, to become an assay cartridge embodying the invention, thereby allowing the reaction to be performed on plasma instead of whole blood, if the physician or user wishes. In some arrangements, a different cap member may be required, depending on whether the extension member is used.

In some embodiments, the extension member may define three wells. The base member may define five or six wells. However, the invention is not limited to any particular numbers of wells in the base member and extension member. In one preferred set of embodiments, the assay cartridge is sized so as to be received by Afinion™ AS100 Analyzer.

The assay cartridge may have some or all of the optional or preferred features described in WO 02/090995. In particular, the extension member may have features of the base member described in WO 02/090995. One, some or all of the wells of the extension member and/or in the base member may have sloping floors, e.g. sloping at an angle of between around 20 to around 40 degrees to the length axis of the well, such as around 30 degrees. One, some or all of the walls of the wells in the extension member and/or in the base member may be transparent so that radiation can be detected through a wall. Corresponding U.S. Pat. No. 7,632,462 is hereby incorporated by reference.

The means for fastening the extension member to the base member could be any suitable fastener. It could be a separate member, such as a wire loop which surrounds the extension member and the base member. However preferably the extension member comprises at least part of the means for fastening the extension member to the base member; e.g. integrally formed with the walls defining the wells.

Such an extension member is inventive in its own right. Thus, from a further aspect, the invention provides an assay cartridge extension member that defines at least one well and comprises means for fastening the extension member to a base member of an assay cartridge.

In any of the foregoing aspects, preferably both the extension member and the base member comprise fastening elements for fastening the two members together. The base member may be arranged to define a channel for receiving a mating projection from the extension member, or the extension member may be arranged to define a channel for receiving a mating projection from the base member. The channel may be elongate, e.g. vertical or parallel to the sides of the wells. It may be defined between two elements or guides. It may be recessed into a wall of the member, or the elements or guides may project outwardly from a wall. One or both of these elements or guides may comprise a flange to retain the mating projection of the other member when it is in the channel. The mating projection may comprise one or more flanges suitable for engaging with one or more flanges on the projecting elements or guides when it is in the channel. The extension member and the base member may be resiliently fastened together at least in part due to a friction fit between the channel and the mating projection.

This arrangement has been found to provide a particularly strong mating, which resists flexing between the two members which could otherwise result in difficulty for an analyser device when manipulating the cartridge. The channel may be open at one end, to allow sliding entry of the mating projection into the channel. The base member and extension member may comprise additional stabilising surfaces which are in mutual contact when the members are fastened so as to prevent relative movement.

In one preferred set of embodiments, a channel is defined vertically and centrally down one wall of the base member (or extension member). The member may further comprise two vertical stabilising surfaces adjacent the outer vertical edges of the wall (vertical being the direction parallel to the wells). The extension member (or base member) may be similarly arranged, with a central mating projection and outer stabilising surfaces, for engaging or contacting the other member.

The channel may comprise a stop at another end, e.g. arranged to contact the mating projection when the extension member and the base member are in a desired fastened position. The cartridge may comprise latching means to fasten the extension member to the base member resiliently when they are in a desired alignment. In some embodiments, one of the members comprises a depression or hole and the other member comprises a sprung or flexible protrusion which can engage in the depression or hole when the members are in a desired position so as to resist a separating force. The latching may be permanent or temporary; the cartridge may or may not comprise means for releasing the latching.

The well openings of the base member and extension member preferably lie in a plane when the two members are fastened. This can facilitate sealing of the wells by foil or by the cap member, and can also simplify manipulation of the assay cartridge by the analyser device.

In one set of preferred embodiments, the base member defines a single line of wells, the extension member defines one well or a line of wells, and the assay cartridge is arranged such that all these wells lie in a line when the extension member is fastened to the base member. This can simplify the design of an analyser device arranged to receive the cartridge by only requiring movement of the pipette relative to the cartridge in a plane containing the line of wells, in order to conduct an assay, rather than requiring relative movement of the pipette in three dimensions. It may, for example, allow an extended assay cartridge to be used in an existing analyser device, such as an Afinion™ AS100 Analyzer, which is advantageous in allowing operation of a known assay cartridge and an extended assay cartridge in the same analyser device.

The pipette may be a capillary-tipped pipette. It may be a membrane-tipped pipette. It is preferably positionable in all the wells of the extension member. The cap member may carry the pipette by releasably supporting all or part of the pipette, or by the pipette being bonded to, or integral with, the cap member. In some embodiments, the assay cartridge comprises a capillary-tipped pipette, detachable from the assay cartridge, for collecting a sample, e.g. of urine or blood. The assay cartridge may alternatively or additionally comprise a membrane-tipped pipette fixed permanently to the cap member. This membrane-tipped pipette may have reagents impregnated in the membrane, which may emit radiation, detectable through a wall of one of the wells, under appropriate conditions; for example, its colour when illuminated by white light may determine the result of an assay. The membrane of the pipette may be angled at an angle of between around 20 to around 40 degrees to the axis of the pipette, e.g. at around 30 degrees.

The cap member may be arranged to carry a magnetic member, positionable in at least one of the wells of the base member and also positionable in the further well of the extension member. This can be useful for performing bead-based assays or magnetic separation. The cap member may have one or more capillary- or membrane-tipped pipettes (or both) in addition to the magnetic member.

The magnetic member may be permanently or removably attached to the cap member. It is preferably elongate. It may comprise a sleeve with a permanent magnet located wholly or partially within the sleeve. The sleeve may be substantially of a plastic material. The sleeve may be a hollow cylinder. It may be of circular cross-section, but is preferably substantially rectangular or square in cross section. It is preferably closed at one end, e.g. at an end furthest from the cap member. The sleeve may be closed at its end by a solid, plastic surface, which may be planar and which may be inclined at an angle of between around 20 to around 40 degrees to an axis of the magnetic member. It may substantially encapsulate a magnet. The magnet preferably fully occupies the interior cross-section of the sleeve, for at least a part of the length of the sleeve; such sizing has been found to give particularly good performance. The magnet may have a sloping face adjacent and parallel to an angled end of the sleeve. This allows the sleeve and the magnet to be fully inserted in any well having a similarly angled base.

Such a magnetic member may be used to isolate analyte in an assay, e.g. to isolate analyte from plasma or whole blood.

Where the cartridge comprises a capillary-tipped pipette, the capillary of the capillary-tipped pipette may be made of any suitable material, but is preferably substantially formed of glass or polymer. Polymer is particularly preferred as this has been found to overcome a problem of glass breakage in the production process.

In preferred embodiments, the capillary comprises, or is substantially made of, a hydrophobic thermoplastic polymer and a hydrophilizing component.

An interior surface (or all surfaces) of the capillary may be treated with a soluble surfactant composition, such as VitroStealth™ (DSM™), or one or more polymerizable gasses, such as with PECVD (e.g. from Plasmatech Inc™). This can increase surface hydrophilicity, thereby ensuring sufficient capillary action to allow the capillary-tipped pipette to draw up a desired amount of fluid from a sample by capillary action. This allows the capillary to be made using synthetic polymer materials, which are usually hydrophobic.

Alternatively and preferably, the polymer may comprise one or more hydrophilic components incorporated into the polymer, e.g. by co-melting. This has been found to be more durable and cheaper than surface coating. Examples of hydrophilic components that may be blended and co-melted with a thermoplastic polymer include antistatic agents such as Hostastat™ HS-1 (Clariant™), CATAFOR™ FL (Rhodia™), Noroplast™ 2002, 3000, 8000, 8500 (Ceca™) and Armostat™ 300, 400, 600, 700, 2000, 2002, 3002 (AkzoNobel™). Other suitable components are disclosed in patent applications WO2006097597 and WO0158987.

In some embodiments, the cartridge comprises a capillary-tipped pipette having a capillary made out of crystal polystyrene, wherein the crystal polystyrene has been post-treated with VitroStealth™ or PECVD, or wherein antistatic agent Armostat™ 2002 has been incorporated with the crystal polystyrene through melting. This has been found to provide particularly rapid capillary filling.

This idea is believed to be new its own right, and thus, from a further aspect, the invention provides a capillary-tipped pipette wherein said capillary tip is made from at least one polymer and a hydrophilic component incorporated into the polymer. The hydrophilic component is preferably incorporated by having been co-melted with the polymer. The optional features described above may be features of this aspect of the invention too, where appropriate.

The cap member is preferably sized to cover, or substantially cover, the wells in the base member and in the extension member, when the base and extension member have been fastened together. The cartridge may comprise one or more seals or stoppers, e.g. an O-ring, between the well-covering cap and well openings in the base member and the extension member.

The means for releasably fastening the cap member to the base member may be any suitable type of fastener. It may be a separate member, such as a wire loop surrounding the cap and the base member. However preferably the cap member and the base member each comprise part of the means for fastening the cap member to the base member; e.g. by providing resiliently deformable projections on the base member which can engage into depressions or holes in the cap member. The cap member may two sets of depressions or holes, defining two different fastening positions; e.g. a fastened position, and an urged-together position in which cutters or stoppers, etc. in the cap member engage more fully with the base member. The assay cartridge may comprise means for fastening the cap member to the extension member, but this is not essential. In fact, in some embodiments it is preferred that the cap member can be separated from the extension member, when the extension member is fastened to the base member, simply by releasing the fastening between the cap member and the extension member, since such a cartridge can then be used in an existing analyser device (e.g. an Afinion™ AS100 Analyzer) without requiring the analyser device to be modified to release an additional fastener acting on the extension member and the cap.

One or more of the wells in each of the base member and the extension member may be foil sealed before use. Two separate foil sheets may be present, one on each member, or wells of both the extension member and the base member may be sealed by a single foil sheet. The latter arrangement may be particularly suitable when the extension member and base member are fastened together in a factory before shipping, for example.

The well-covering cap member is preferably equipped with foil seal cutters for cutting the well-covering foil seal or seals to permit the pipette, which is positionable in the wells, actually to be inserted into the wells.

The applicant has realised that cutters in the cap member as described in WO 02/090995, and other known designs for assay-cartridge foil cutters, are undesirable in at least some embodiments of the present invention, because they can place excessive strain on the analyser device, such as an Afinion™ AS100 Analyzer, due to the larger number of wells which may be present in an extended cartridge. This may, over time, lead to damage to the device.

Therefore the cap member preferably comprises a cutter comprising two blades for shearing a foil seal covering a well of the base member or extension member, wherein each blade is arranged to shear the foil adjacent a respective wall of the well. The two respective walls are preferably parallel walls on opposite sides of the well. Each blade is preferably linear and the two blades are preferably parallel to each other. The cutter preferably comprises a third blade extending between the two shearing blades, for cutting the foil along a line between the two walls. This blade is preferably linear and substantially perpendicular to the two shearing blades. It is preferably spaced away from the ends of the shearing blades. In some preferred embodiments, the three blades are in an approximately H-shaped configuration.

The well opening may be substantially rectangular, and the cutter may be arranged to cut the foil cover so as to form two rectangular flaps, each of substantially half the area of the well opening. The cutter may be shaped so as to fold two flaps of foil into the well, e.g. to lie parallel to and touching respective walls of the well. Blades of the cutter comprise one or more straight or curved cutting edges. In one set of embodiments, the cutter has three blades, e.g. as described above, each having two straight cutting edges. One or both of the shearing blades preferably has two cutting edges which meet at a point, pointing away from the cap member (i.e. towards the foil, when in use). The third blade (if present) preferably has two cutting edges, each of which rises away from the cap member to reach a respective one of the points on the shearing blades.

The applicant has found that shearing the foil along two walls of the well requires less force to be applied to the cutter than is the case for certain other arrangements such as having four cutting edges which meet at a central point and pierce the foil in the centre of the well opening. Preferably the assay cartridge is such that a force of less than 20 N is sufficient to urge the cap member towards the base and extension members so as to cut open the foil of all foil-covered wells in the base and extension members. This can prevent excessive wear to known analyser devices, which may damage the devices over time. Cutting the foil so that it forms two flaps rather than one single flap, is also advantageous in limiting how far the foil extends towards the base of the well, when folded into the well by the cutter, thereby avoiding potential interference with reagents in the well.

This design of cutter may also be used with known assay cartridges to obtain the same benefits. Thus, from a further aspect, the invention provides a cutter for an assay cartridge comprising a base member defining two or more wells and a cap member arranged to carry a pipette positionable in at least two of said wells, wherein the cutter comprises two blades for shearing a foil seal covering one of the wells, the two blades being linear and parallel to each other, and a third blade extending between the two shearing blades, spaced away from the ends of the shearing blades. This aspect extends to an assay cartridge comprising such a cutter.

The cutter may be located in, or form part of, the cap member. The assay cartridge may be a cartridge as described in WO 02/090995 or an Afinion™ cartridge as sold by Axis-Shield™. Any optional feature of the earlier aspects may be an optional feature of this cutter or assay cartridge.

In any of the foregoing aspects, the cap member may be provided with resilient material at one or more positions corresponding to the tops of some or all of the wells (e.g. just the liquid containing wells) in the base member and extension member, such that when cap member is urged towards the base and extension members, a liquid-tight seal is formed at the well tops. Such material may for example be a layer coated onto the cap member, or discs or gaskets attached (e.g. welded or adhered) to the cap.

This material, or seal, may comprise a plurality of contiguous lengths, each having this cross-section, arranged to conform to some or all of the walls defining a well opening in the base or extension member (e.g. a square, rectangle or circle). The seal may be arranged to compress against a surface of the base or extension member adjacent the well-walls when the cap member is urged towards the base or extension member, thereby forming or contributing to the formation of a liquid-tight seal for the well.

Figure 13:
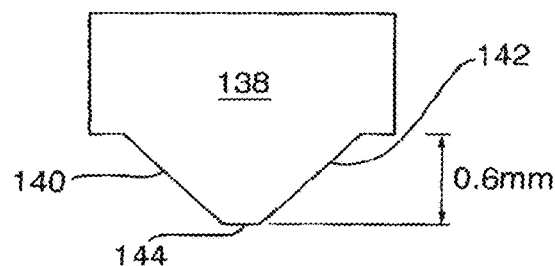

A cross-section through a known seal 138 is shown in FIG. 13. A pair of sloping faces 140, 142 extend towards each other, away from the cap member. They are connected by a horizontal edge 144, which is arranged so as to make first contact with a base member when the cap member is urged towards the base member.

Such a seal may be used in embodiments of the present invention. However the applicant has realised that this can have shortcomings where the seal extends around wells in both the base member and the extension member. This is because the pressure with which the analyser device must urge the cap member onto both a base member and extension member is typically greater than that required for a similarly-sized base member without the extension; however, such pressures may put excessive strain on the analyser device. For example, it is undesirable for an Afinion™ AS100 Analyzer to be required to apply more than 20 N, or else the device may become damaged over time.

Accordingly, in a preferred set of embodiments, the cap member comprises an elongate, resiliently-deformable seal with a cross-section which comprises at least one, and preferably two, concave curved edges. The seal thus comprises one, two or more elongate, concave faces. These faces preferably approach one another, away from the cap member. They are preferably connected by a horizontal edge, which is arranged so as to make first contact with a base member when the cap member is urged towards the base member. The curves may be symmetrical, but are preferably asymmetrical; e.g. with one being closer to a rounded right-angled bend and with the other being closer to a circular arc. Such an arrangement has been found to require a particularly low force in order to compress the seal by an amount suitable for sealing the wells (e.g. 0.2-0.3 mm of compression in some embodiments). In particular, substantially less force is required than with the seal shown in FIG. 13.

This design of seal may also be used advantageously with known assay cartridges, where the reduced force required to compress the seal can reduce wear on the analyser device. Thus, from a further aspect, the invention provides a seal for an assay cartridge, wherein the seal is elongate and resiliently-deformable, with a cross-section which comprises at least one, and preferably two, concave curved edges. The seal may have any of the previously-described optional features. This aspect extends to an assay cartridge comprising such a seal.

In any of the foregoing aspects, the extension member may comprise a glass filter located at the base of a well in the extension member. A filtering action may be provided when a membrane-tipped pipette of a cartridge is pressed against the glass filter and a negative pressure is applied to the pipette. By providing a double layer of the glass filter and a microporous membrane in an assay cartridge, the risk of blood-cell contamination and haemolysis can be reduced.

In any of the foregoing aspects, the extension member may comprise a magnet. The magnet may be located at the bottom of a well of the extension member, or may be located adjacent the inside wall of a well of the extension member. A sample containing a targeted analyte may be mixed with a specific binding partner conjugated to a paramagnetic substrate, e.g. paramagnetic microspheres. Such mixing preferably occurs in a well that is distanced from the magnet, e.g. spaced apart from a well containing the magnet by a third well, so as to be substantially outside the influence of the magnetic field of the magnet. This mixing well may be in the extension member. After a suitable incubation time, the mixture may be transferred to a well within the influence of the magnetic field of the magnet, such that the targeted analyte may be isolated from the sample. The isolated analyte may, after washing, be released from its specific binding partner, e.g. by a decreased pH, and further processed (e.g. in a well of the base or extension member), or it may be further processed still bound to the specific binding partner (e.g. by reagents from the base member).

From another aspect, the invention provides an assay method comprising use of an assay cartridge as described herein. The method may comprise assaying for an analyte in a biological sample or for a property of a biological sample, e.g. to assay for cholesterol (CH) and/or triglyceride (TG) and/or high-density lipoprotein (HDL) levels in a blood or blood-derived sample.

From a further aspect, the invention provides an assay method using an assay cartridge which comprises:
 a base member that defines at least two wells;
 a pipette positionable in at least one of said wells;
 a cap member arranged to carry the pipette;
 means for releasably fastening the cap member to the base member;
 an extension member that defines at least one further well; and
 means for fastening the extension member to the base member such that, when the extension member is fastened to the base member, the pipette is positionable in at least one of the wells of the base member and is further positionable in the further well of the extension member,
wherein the method comprises positioning the pipette in a well in the base member at a first time, and positioning the pipette in a well in the extension member at a second time. A sample or reagent may be transferred from the pipette into the well in the base member, or vice versa. Similarly a sample or reagent may be transferred from the pipette into the well in the extension member, or vice versa.

Optional or preferred features of any aspect or embodiment described herein may be optional or preferred features of any other aspect described herein, wherever appropriate.

Figure 2:
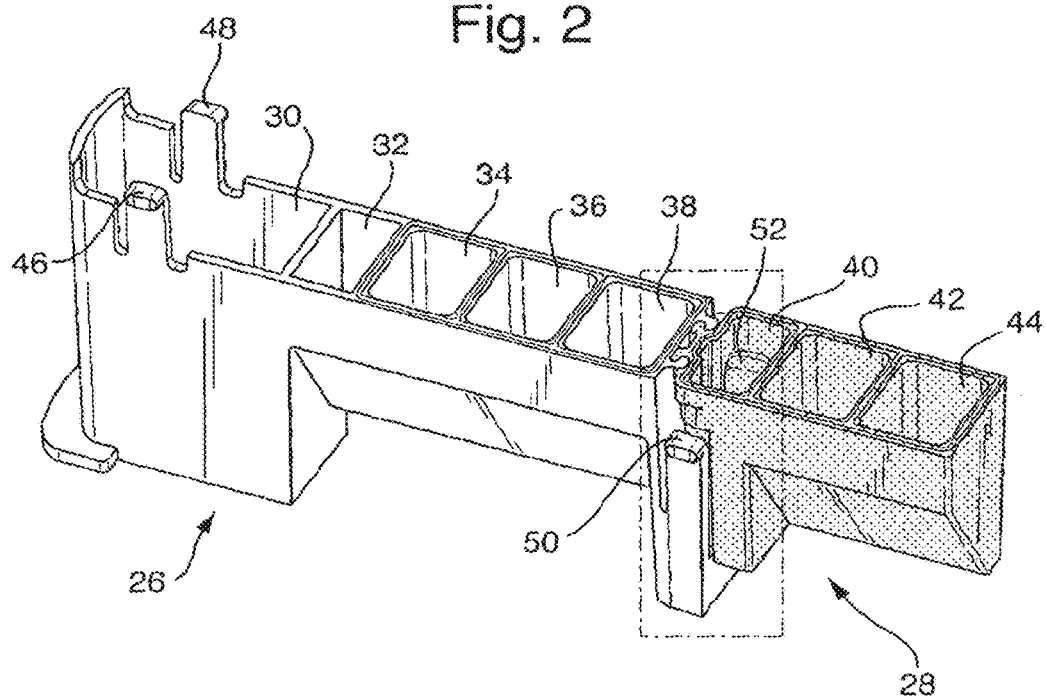
Figure 3:
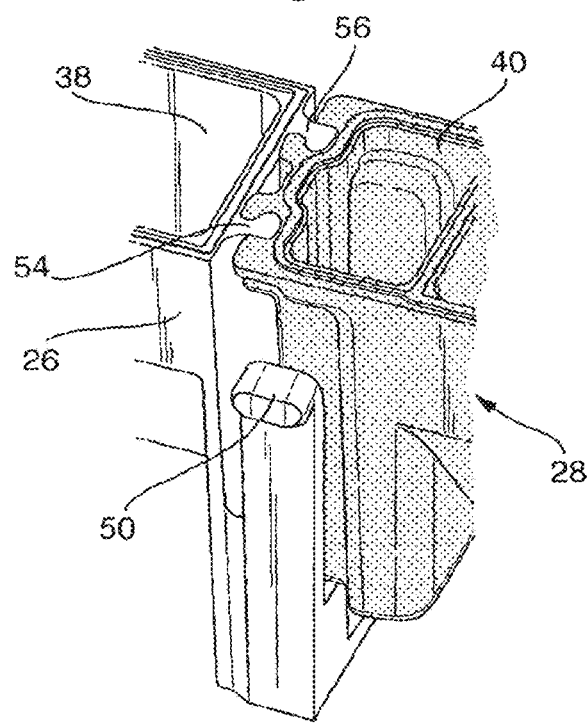
Figure 4:
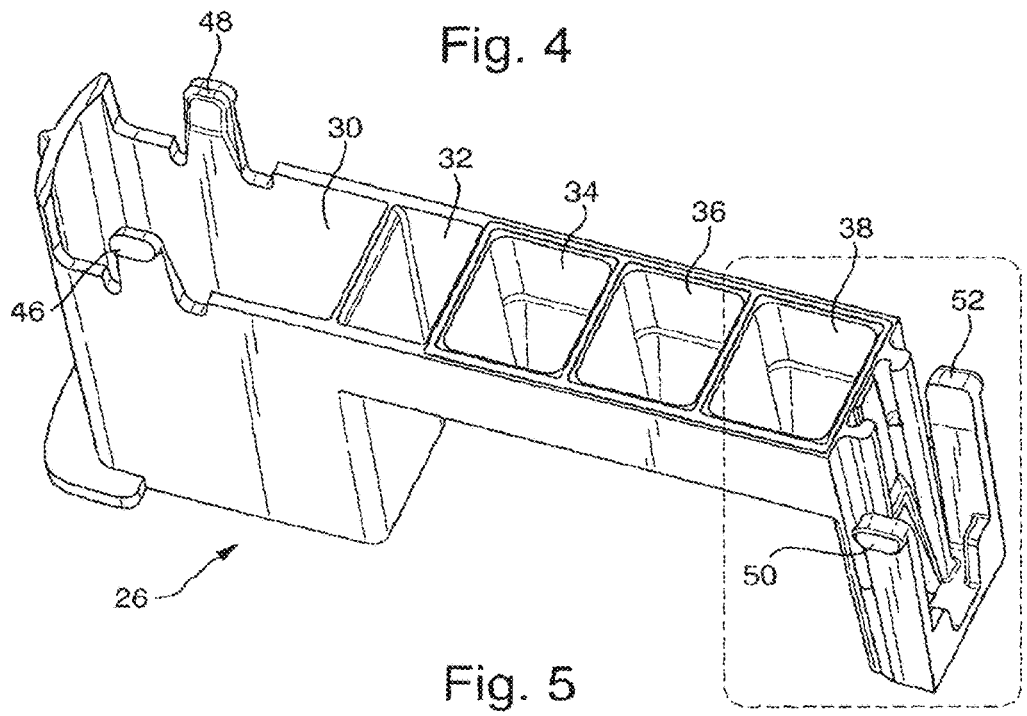
Figure 5:
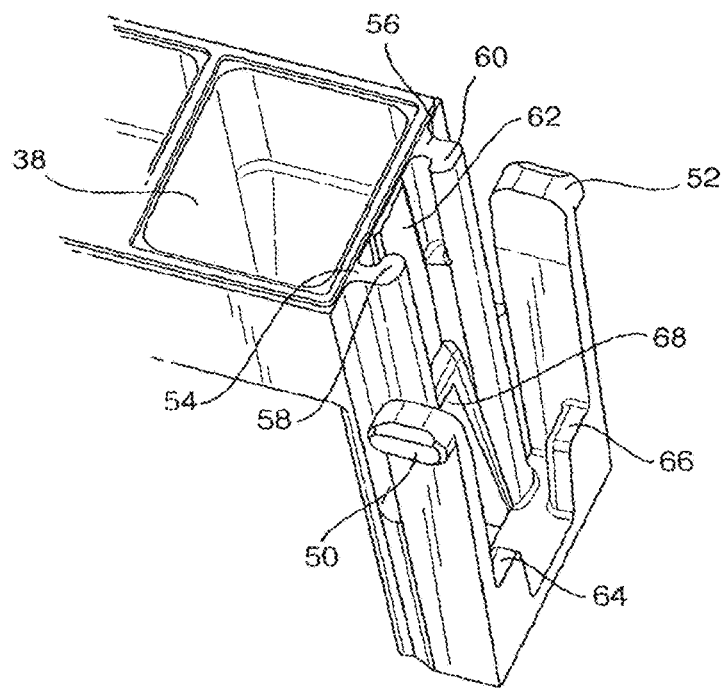
Figure 8:
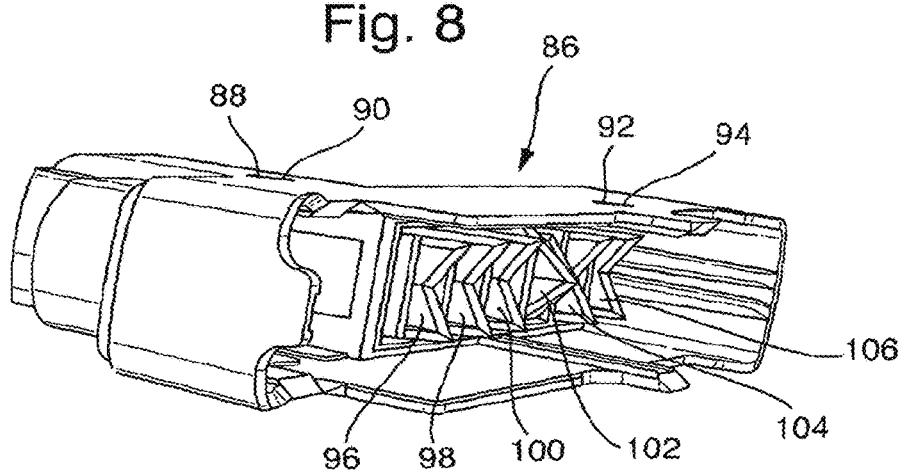
Figure 9:
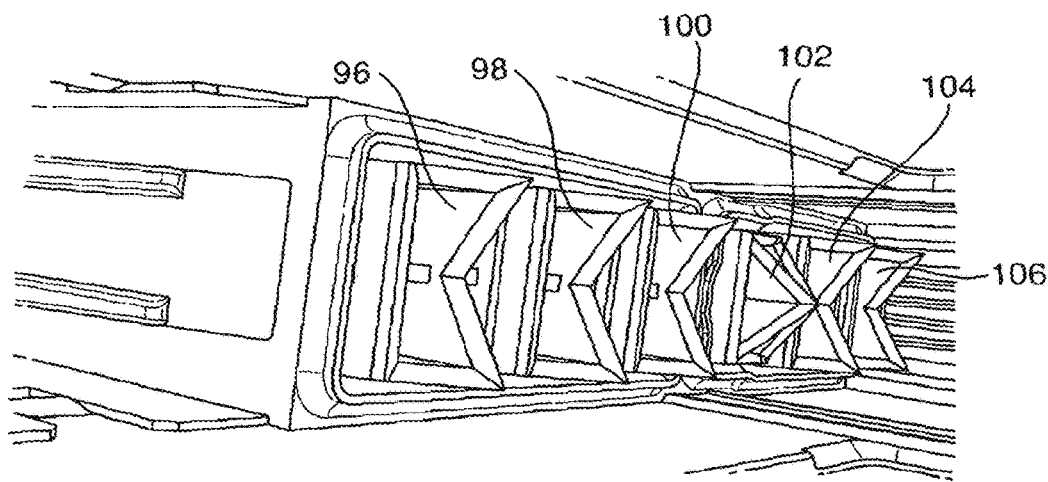
Figure 10:
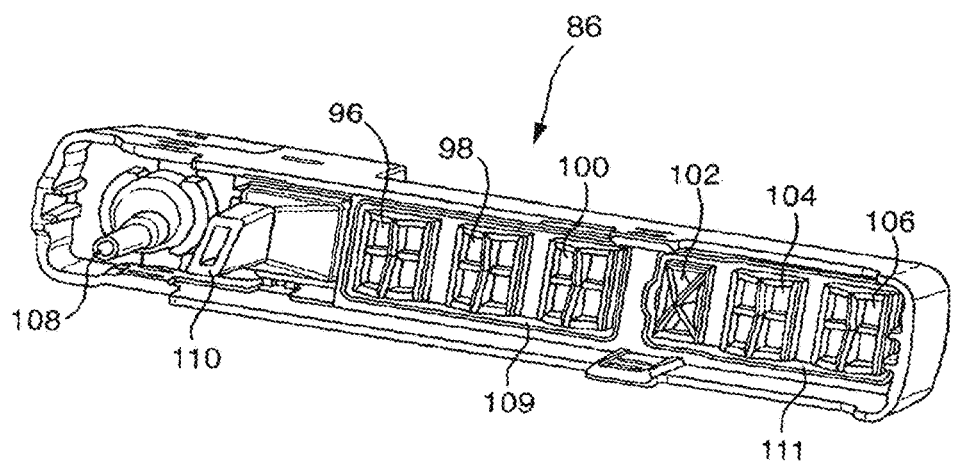
Figure 11:
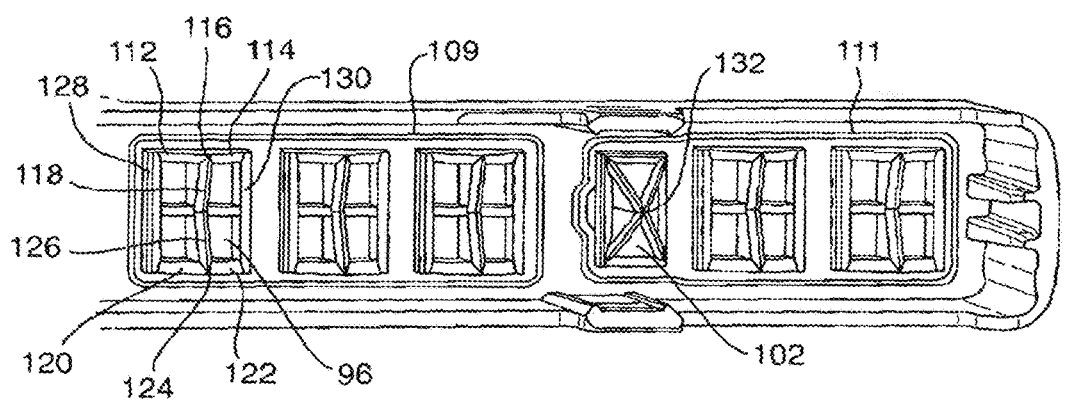
Figure 12:
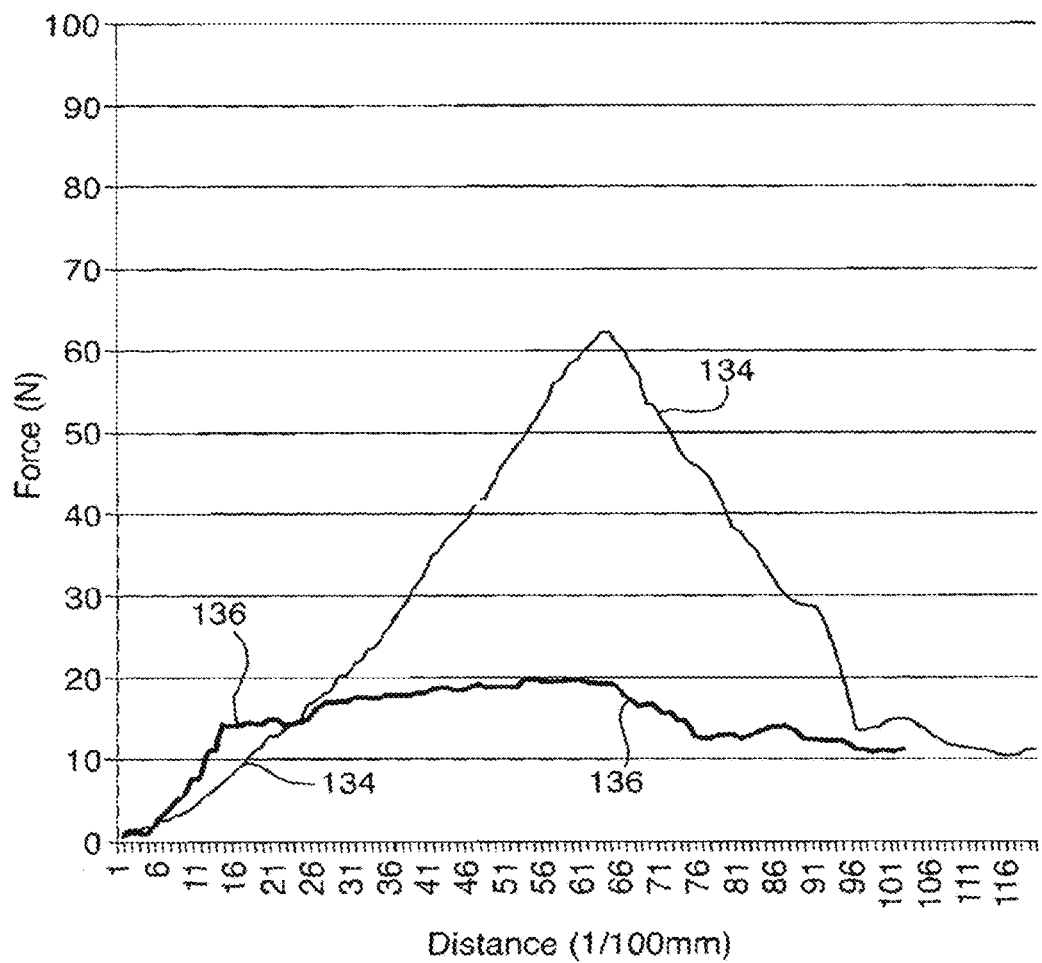
Figure 14:
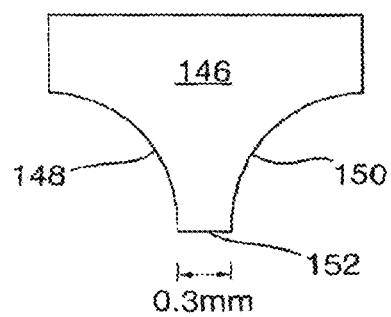
Figure 15:
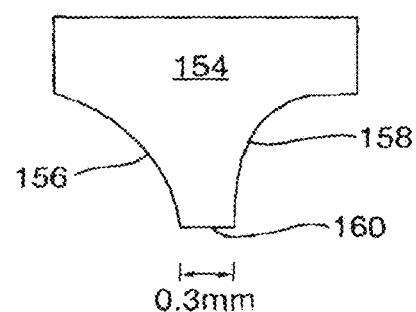
Figure 16:
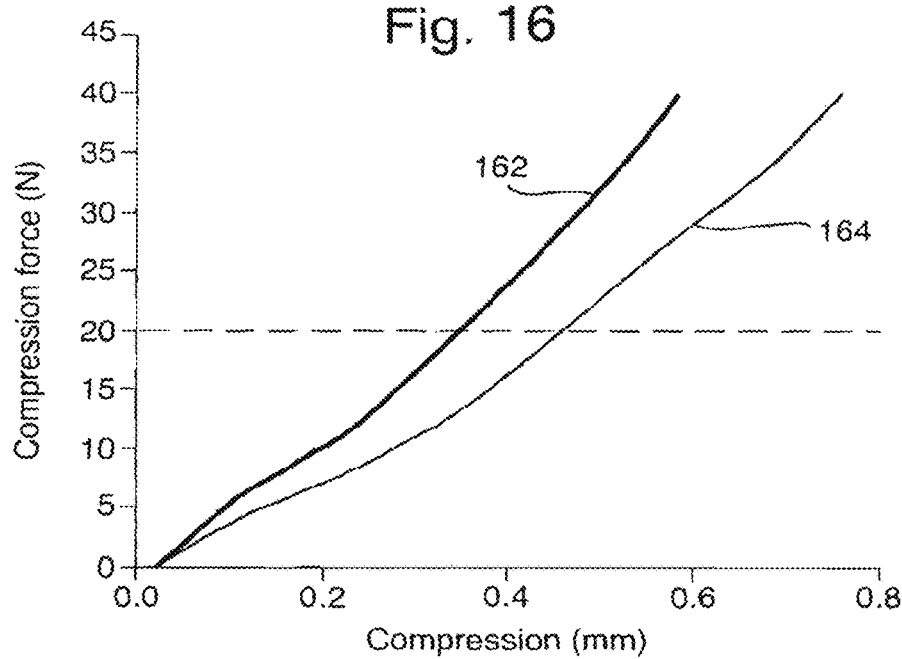
Figure 17:
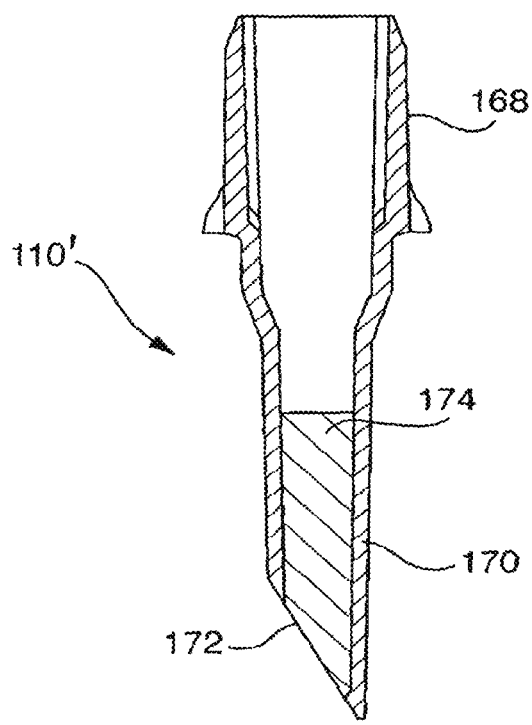
Figure 18:
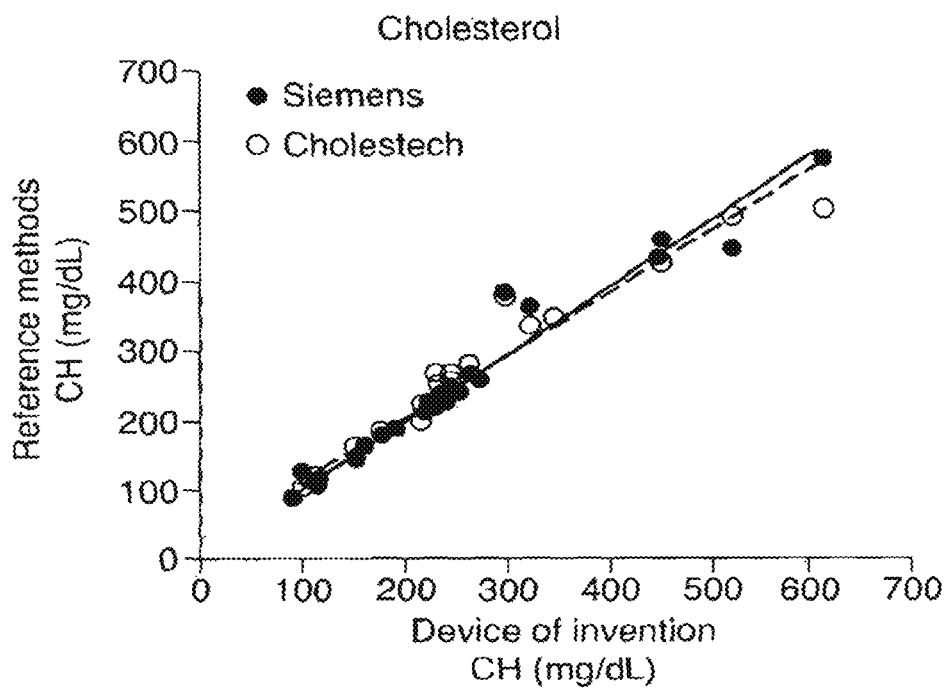
Figure 19:
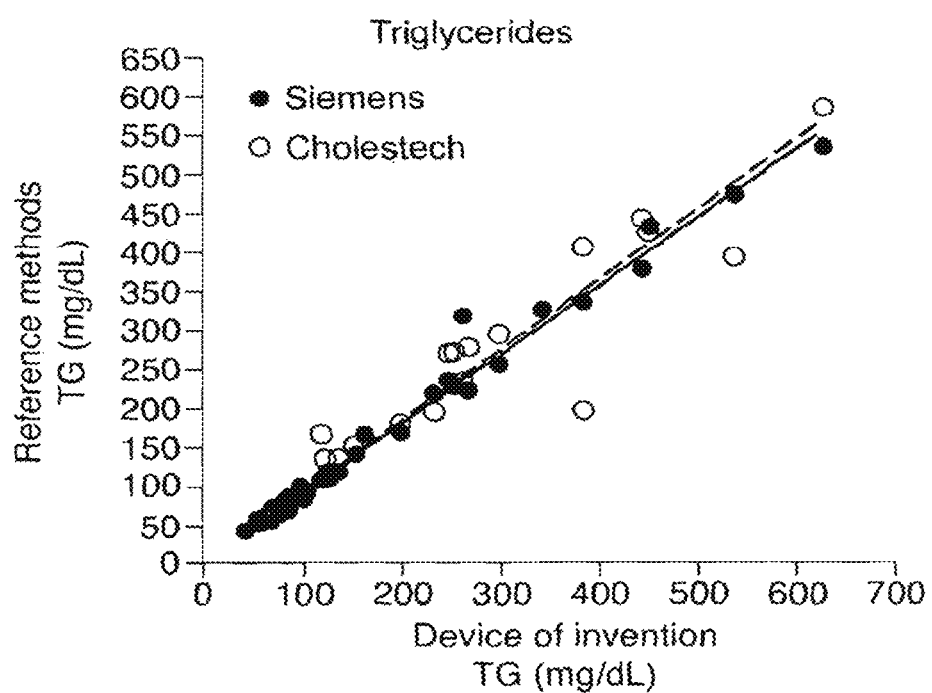

Certain preferred embodiments of the invention will now be described, by way of example only, with reference to the accompanying drawings, in which:

FIG. 1 is a perspective view of a prior-art cartridge;
FIG. 2 is a perspective view of a base member fastened to an extension member embodying the invention;
FIG. 3 is a close-up of part of FIG. 2;
FIG. 4 is a perspective view of the unconnected base member;
FIG. 5 is a close-up of part of FIG. 4;
FIG. 6 is a perspective view of the unconnected extension member;
FIG. 7 is a further perspective view of the unconnected extension member;
FIG. 8 is a perspective view of the underside of a lid member for use with the base member and extension member;
FIG. 9 is a more-detailed perspective view of part of the lid member;
FIG. 10 is a different perspective view of the lid member;
FIG. 11 is a further perspective view of part of the lid member;
FIG. 12 is a graph relating to the force required to cut a foil seal for two difference cutter designs;
FIG. 13 is a cross-section through a prior-art seal;
FIG. 14 is a cross-section through a seal embodying the invention;
FIG. 15 is a cross-section through a different seal also embodying the invention;
FIG. 16 is a graph relating to the force required to compress the seals depicted in FIG. 13 and FIG. 15;
FIG. 17 is a vertical cross-section through a magnetic member for use with a cartridge embodying the invention;
FIG. 18 is a graph of experimental results comparing an embodiment of the invention with available systems for determining cholesterol;
FIG. 19 is a further such graph for triglycerides;
FIG. 20 is a further such graph for HDL;
FIG. 21 is a further such graph for computed LDL;
FIG. 22 is a dose-response graph for BNP levels measured using a cartridge embodying the invention; and
FIG. 23 is a BNP levels measured using a different cartridge embodying the invention.

FIG. 2 shows a base member 26 and an extension member 28 which embody the invention. The base member 26 is former of a transparent plastics material. The extension member 28 is shown with different shading to aid identification, but may be made of the same transparent plastic. In alternative embodiments, one or both members may be opaque. The base member 26 defines a line of five wells 30-38, four of which 32-38 have sloping bases. The first well 30 is principally a storage area for a capillary-tipped pipette (not shown), and the second well 32 is principally a storage area for a membrane-tipped pipette (not shown).

The extension member 28 defines three wells 40, 42, 44 in a line. The second 42 and third 44 of these have sloping bases. The wells 40, 42, 44 in the extension member 28 and the second to fifth wells 32-38 in the base member 26 are principally intended to contain reagents when the assay cartridge is in use and optionally when the cartridge is in storage.

The base member 26 has four flexible, upward projections having flanged tips 46-52 which can snap into through-holes in a cap member (not shown) to fasten the base member 26 to the cap member.

FIG. 3 shows the mating connection between the base member 26 and the extension member 28 in greater detail. Two elongate, vertical projections 54, 56 from the extension member 28 can be seen.

FIG. 4 shows the base member 26 separate from the extension member 28.

FIG. 5 shows, in greater detail, the elements of the mating connection which are on the base member 26. Each of the two elongate, vertical projections 54, 56 has a flange along its outer length which curves towards the other projection, thereby defining a vertical channel 62 between the projections 54, 56. A pair of upwardly extending plates 64, 66 towards the bottom of the base member 26 act both as height stops, by preventing movement of the extension member 28 below their upper faces, and as tilting stops to resist tilting movement of the extension member 28 away from the base member 26. The underside of a small projection 68 located centrally between the two vertical projections 54, 56 and approximately half way up the end face of the base member 26 acts as a locking hook for retaining the extension member 28 when it is fastened to the base member 26.

FIGS. 6 and 7 show the extension member 28 separate from the base member 26. The extension member 28 also has two elongate vertical projections 70, 72, each of which has a flange 74, 76 along its outer length which curves away from the other projection. The vertical projections 70,72 are closer to each other than the projections 54, 56 on the base member 26 and are sized such that they can slide into the channel 62 defined between the base member's projections 54, 56. The two sets of projections and flanges can form an interference fit when the extension member 28 is fastened to the base member 26. The vertical projections 54, 56, 70, 72 may be only substantially vertical, and may instead taper together slightly towards the bottom of the members 26, 28 so that the strength of the interference fit increases as the extension member 28 is lowered relative to the base member 26. The interference fit may be fairly gentle in some embodiments, since other means are provided for retaining the base member 26 and extension member 28 in the desired position once fastened.

FIG. 8 shows a cap member 86 lying on its side. The pipettes are not shown for ease of understanding. The cap member 86 is sized to cover the joined base member 26 and extension member 28 shown in FIG. 2 when fastened. The sides of the cap member 86 can overhang the sides of the joined base and extension members in all directions.

The cap member 86 has eight through-holes in its side walls, four of which 88-94 are visible in FIG. 8. The four flanged tips 46-52 of the base member 26 can engage in either the lower 90, 94 or upper 88, 92 sets of through holes to fasten the cap member 86 to the base member 26 in either a fastened position in which the cap is relatively distanced from the base member, or in an urged-together position in which they are relatively close.

A line of six downward-facing cutters 96-106 is situated along an inner horizontal surface of the cap member 86, to align with the third to fifth wells 34-38 of the base member 26 and the three wells 40-44 of the extension member 28. These six wells are initially sealed by foil sheeting (not shown), which the cutters are arranged to cut open when the cap member 86 is urged into the urged-together position.

FIG. 10 shows the cap member 86 including a capillary-tipped pipette 108 and a membrane-tipped pipette 110, which are arranged to be positioned in the first and second wells 30, 32 of the base member 26 respectively when the cap member 86 is fastened to the base member 26. Also visible is an elongate, downwardly-protruding rubber seal 109 surrounding the first three cutters 96-100, and another, similar seal 111 surrounding the next three cutters 102-106. The seals may be bonded to, or formed with, a backing sheet which connects between the two.

FIG. 11 shows a detailed view of the cutters, looking vertically upwards from underneath. The first, second, third, fifth and sixth cutters 96, 98, 100, 104, 106 are of identical design, while the fourth cutter 102 is different. The first cutter 96 is rectangular in outline and has three linear blades each having two cutting edges. One pair of cutting edges 112, 114 is situated along a short edge of the rectangle. The edges 112, 114 slope downwards to a point 116 away from the bulk of the cap member 26. Another pair of cutting edges 120, 122 is situated along the other short edge of the rectangle and similarly slope downwards to a point 124. The contiguous cutting edges 118, 126 of the third blade form a line joining the midpoints of the short edges; one edge 118 slopes downwards to meet the first pair of edges 112, 114 at the first point 116. The other edge 126 slopes downwards to meet the second pair of edges 120, 122 at the second point 124.

The fourth cutter 102 has four cutting edges which meet at a central point 132. It acts to pierce the foil centrally. It is of different design because the corresponding well has a smaller opening, for which the three-blade cutter is less well suited.

In use, the assay cartridge may be received by the end-user (e.g. a physician) with the extension member 28 fastened to the base member 26 and with the cap member 86 fastened to the base member 26 in its higher, fastened position. The third to fifth wells 34-38 of the base member 26 and the three wells 40-44 of the extension member are initially sealed by one or more foil sheets stretched across their openings and bonded to an upper surface of the walls defining the wells. Some or all of the wells may contain reagents, e.g. as described in the Examples below.

A physician can remove the capillary-tipped pipette 108 from the cap member 86, collect a sample in the pipette (e.g. of blood), replace the pipette in the cap member 86, and load the cartridge into as analyser device (e.g. an Afinion™ AS100 Analyzer). The analyser device will urge the cap member 86 towards the base member 26. This causes the first cutter 96 to shear the foil seal along the shorter edges of the rectangular opening of the third well 34, shearing from the mid-point of the short edge outwards, as well as to cut a line along the middle of the foil, parallel to the longer edges of the rectangle. Ridges 128, 130 along the long edges of the cutter 96 push the two flaps of foil against the inside edges of the well 34. The other identical cutters act similarly. The fourth cutter 102 pierces the foil centrally and creates four flaps.

The analyser device may then release the cap member 86 from the base member 26 and move it relative to the base and extension member 26, 28 so as to position the capillary-tipped and membrane-tipped pipettes 108, 110 in various of the wells as necessary for carrying out the desired assay. The operation of the analyser device in this respect is substantially as described in WO 02/090995. Once the assay is complete, the cap member 86 is again fastened to the base member 26 in the urged-together position, thereby causing the seals 109, 111 to compress and form a fluid-tight seal around the wells, preventing leakage of used reagents from the cartridge.

FIG. 12 shows a graph of the urging force, against displacement, required to be exerted to move the cap member 86 into the urged-together position when the cutters are cutting the foil seals. The upper line 134 shows the force required when the cutters all have a piercing design similar to that of the fourth cutter 102. The required force exceeds 60 N. The lower line 136 shows the force required when the cutters are as described in FIGS. 10 and 11. This force never exceeds 20 N.

FIG. 13 shows a prior-art seal design, as already described.

FIGS. 14 and 15 show cross-sections through two different designs for the seals 109, 111, both embodying the invention. In the first design, a pair of concave, curved faces 148, 150 extend towards each other, away from the cap member 86. They are connected by a horizontal edge 152. The curves 148, 150 are mirror images. In the second design, a pair of concave, curved faces 156, 158 again extend towards each other, away from the cap member 86. They are connected by a horizontal edge 160. However, here the curves 156, 158 are not mirror images, but are defined by dissimilar equations. This asymmetry has been found to provide particularly good performance.

FIG. 16 plots the urging force, against displacement, required to move the cap member 86 into the urged-together position when compressing the seals 109, 111 against the base and extension members 26, 28. The upper line 162 shows the force required when the seal has a known design as shown in FIG. 13. The lower line 164 shows the force required when the seals are as described in FIG. 15. It will be seen that the compression is significantly greater for the same force when using the design embodying the invention.

FIG. 17 shows a magnetic member 110' belonging to an assay cartridge that is like the cartridge depicted in FIGS. 2-11 but with the membrane-tipped pipette 110 (shown in FIG. 10) replaced by the present magnetic member 110', which is similarly sized and shaped. The magnetic member 110' is elongate, having a wider top section 168 for connection to the cap member and a narrower sleeve section 170. The sleeve section 170 is a hollow cylinder of rectangular cross-section 168. It is closed at one end by a sloping planar face 172. The sleeve section 170 and sloping face 172 may be of plastics material. The sleeve section 170 contains within it a permanent magnet 174 that spans the widths of the sleeve and occupies the majority of the length of the sleeve section 170.

Some example assays using cartridges embodying the invention are now described.

The wells in the extension member 28 of FIG. 2 may carry reagents; alternatively these wells can carry calibrators (liquid or freeze-dried), harbour a blood separation unit, a wiper (to minimize cross-contaminations in assays measuring a plurality of analytes), or have other functions. The base member 26 and extension member 28 may be snapped together by the manufacturer and sealed with foil as one unit in the assembly line, or treated and sealed separately to be snapped together by the customer.

EXAMPLE 1

An enzymatic assay using the base member 26 can be performed as follows. 15 μL of serum or plasma is drawn into the capillary-tipped pipette 108 by capillary forces and the capillary-tipped pipette 108 placed in the cartridge. The cartridge is inserted into an Afinion™ analyser device. In the instrument, the capillary-tipped pipette 108 is moved to the fifth well 38 and the sample mixed with dilution buffer, typically 250 μL. The third and fourth wells 34, 36 are prefilled with reagent 1 and 2 for the analysis of analytes 1 and 2, typically 100-150 μL of reagent. Blank readings are performed on reagents and diluted sample. The capillary-tipped pipette 108 transfers diluted sample (typically 50 to 100 μL) third and fourth wells 34, 36, and sample and reagent are mixed. Depending on analyte measured a second blank reading may be performed. Reaction mixtures are heated. Depending on measurement mode (end-point, fix-point or kinetic reading) one or several readings are performed. Readings are transformed to concentrations by interpolation from calibration curves present in the barcode of the cartridge.

EXAMPLE 2

Cholesterol (CH) and triglyceride (TG) levels of nine serum samples were measured on an Afinion™ analyser device essentially as described in Example 1. The calibration curve used was constructed from 6 calibrators that had been previously quantified at a CRMLN laboratory (Seattle, USA). In parallel the same nine samples were measured by a commercial point-of-care analyzer, Cholestech™ LDX system (Lipidprofile-Glu), and on a clinical laboratory instrument ADVIA 2400, using Siemens™ reagents, each using a calibrator system supplied by the manufacturer. Obtained values are given in Table 1

TABLE 1

| | Cholesterol (mg/dL) | | | Triglycerides (mg/dL) | | |
|---|---|---|---|---|---|---|
| Sample | Afinion | Cholestech | Siemens | Afinion | Cholestech | Siemens |
| 11-1487 | 156 | 167 | 157 | 101 | 111 | 106 |
| 11-1488 | 162 | 163 | 162 | 110 | 104 | 107 |
| 11-1489 | 161 | 170 | 166 | 61 | 56 | 64 |
| 11-1491 | 221 | 220 | 224 | 191 | 194 | 182 |
| 11-1491 | 167 | 174 | 168 | 75 | 68 | 73 |
| 11-1492 | 202 | 189 | 204 | 74 | 59 | 71 |
| 11-1493 | 173 | 175 | 172 | 97 | 97 | 97 |
| 11-1494 | 215 | 241 | 222 | 285 | 304 | 277 |
| 11-1495 | 268 | 261 | 253 | 110 | 116 | 109 |

EXAMPLE 3

CH, TG and HDL levels of 42 plasma samples were measured in an Afinion™ analyser device essentially as described in Example 2 with the assay cartridge extended with a three-well extension unit embodying the invention (similar to that depicted in FIG. 6). The cartridge now also contained two HDL reagents, one for blocking non HDL and one for converting HDL to detectable product. As in Example 2, the plasma samples were also measured with the Cholestech™ LDX Lipidprofile-Glu and Siemens™ Advia systems. FIGS. 18-21 compare the three methods with respect to obtained values for CH, TG, HDL, and LDL. LDL was not directly measured but computed from the other variables using the Friedewald equation:

$$LDL = CH - HDL - TG/5 (\text{in mg/dL}).$$

EXAMPLE 4

A whole blood sample was filtered in an extended assay cartridge embodying the invention (similar to that depicted in FIG. 2), in which one of the wells contained a glass filter attached to the well bottom. The sample was run in 6 replicates. Whole blood was drawn into a 15 μL capillary-tipped pipette by capillary forces and inserted into the extended cartridge. The sample was emptied and mixed in 285 μL dilution buffer. 200 μL was transferred by the capillary-tipped pipette to the glass filter containing well. The membrane-tipped pipette was then positioned tightly over the glass filter. When below ambient pressure was applied to the open end of the membrane-tipped pipette the diluted whole blood flowed into the glass filter and whereas blood cells were trapped in the filter the diluted plasma flowed through the filter and the microporous membrane into the membrane-tipped pipette. When the pressure started rising (sucking air), the membrane-tipped pipette was removed from the glass filter, lowered into an empty well and forced to release the filtered plasma by applying an above ambient pressure. Blood contamination was measured after converting contaminating hemoglobin to methhemoglobin using $NaNO_2$ and measuring the absorbance at a wavelength of 410 nm. The absorbance was converted to % Hb by interpolation from a calibration curve constructed from known concentrations of methhemoglobin. Results are shown in Table 2.

TABLE 2

| Run# | % Hb contamination | Mean ± SD |
|---|---|---|
| 1 | 1.23 | 1.24 ± 0.07 |
| 2 | 1.16 | |
| 3 | 1.27 | |
| 4 | 1.29 | |
| 5 | 1.32 | |
| 6 | 1.15 | |

EXAMPLE 5

Triglycerides and total cholesterol are determined using end-point measurements, but cholesterol associated with HDL does not produce a measurable end-point and must be determined using fix-point or kinetic measurement. Whereas end-point measurement renders the measurement largely independent of reagent activity, fix-point or kinetic measurements are highly dependent upon reagent activity. It is therefore recommended that such assays use calibrators to compensate for any reagent degradation.

TABLE 3

Reagents and volumes of assay cartridge

| Well nr. | Content | Volume |
|---|---|---|
| 3rd | CH reagent | Typically 100 μL |
| 4th | TG reagent | Typically 100 μL |
| 5th | Dilution buffer | Typically 150 μL |
| 6th | HDL reagent 1 | Typically 350 μL |
| 7th | HDL calibrator | Freeze dried |
| 8th | HDL reagent 2 | Typically 100 μL |

15 μL of serum or plasma is drawn into the capillary-tipped pipette by capillary forces and placed in the extended assay cartridge shown in FIGS. 2-11, where the extension member is transparent. The cartridge is inserted into an Afinion™ analyser device. In the instrument, the capillary-tipped pipette 108 is moved to the fifth well 38 and mixed with dilution buffer. 150 μL HDL reagent 1 is transferred from the sixth well 40 to the seventh well 42 containing the freeze dried HDL calibrator. Diluted sample (typically 30 μL each) is added to the sixth, fourth and third wells 40, 36, 34. While the enzymatic reactions which produce measurable end-points are running in the third and fourth wells 34, 36, nonHDL in sample (sixth well 40) and calibrator (seventh well 42) are being blocked by the R1 reagent. After sufficient time to block nonHDL has passed (typically 2 minutes), HDL R2 (typically 50 μL) is transferred from the eighth well 44 to the seventh well 42, and nonHDL-blocked sample (typically 150 μL) is transferred from the sixth well 40 to the eighth well 44. The reactions in the seventh and eighth wells 42, 44 are monitored through a transparent side of the extension member to determine the absorption increase and end-points are measured in the third and fourth wells 34, 36.

Absorptions are converted to concentrations by interpolation from pre-established calibration curves supplied in the barcode of the cartridge. The absorption increase of the calibrator is used to correct the HDL calibration curve for any age related reagent degradation.

EXAMPLE 6

B-type Natriuretic Peptide (BNP) levels in six samples spanning 0 to 100 pg/mL were measured in replicates in an Afinion™ analyser device with an extended assay cartridge embodying the invention, similar to that depicted in FIG. 2, but without the membrane-tipped pipette 110 shown in FIG. 10 and with the extension member being made from a transparent polymer material. A magnet was located in the sixth well 40. Reagents and volumes are given in Table 4. Sample (15 μL) was allowed to react with the Reagent Formulation (5 μL) of eighth well 44, containing anti-BNP antibody 1 conjugated to 0.5 μm paramagnetic particles (1.25%) and 0.2 μm latex particles coated with HRP and anti-BNP antibody 2 (0.3%). Formation Anti-BNP 1-BNP-anti BNP 2/HRP complex was allowed to proceed for 10 minutes at ambient temperature, then wash buffer (100 μL) was added and the mixture transferred to the seventh well 42. The paramagnetic particles of the Reagent Formulation, including bound BNP/anti-BNP2/HRP, were attracted to the wall between seventh well 42 and the sixth well 40 by the magnet. Unbound anti-BNP 2/HRP was removed and the trapped paramagnetic particles with complexes were washed five times with 150 μL of wash buffer. Finally 150 μL TMB was added to the seventh well 42 and the absorption increase monitored for 750 s at 625 nm. FIG. 22 shows the dose-response graph obtained. The achieved Limit of Detection was 5 pg/mL.

TABLE 4

Reagents and volumes of BNP assay

| Well nr. | Content | Volume |
|---|---|---|
| | Base member | |
| 3rd | TMB solution | 300 μL |
| 4th | Wash buffer | 400 μL |
| 5th | Wash buffer | 475 μL |
| | Extension member | |
| 6th | Magnet | |
| 7th | Partitioning vessel | |
| 8th | Reagent Formulation | 5 μL |

EXAMPLE 7

BNP levels in five samples spanning 0 to 100 pg/mL were measured in replicates in an Afinion™ analyser device with an extended assay cartridge embodying the invention, similar to that depicted in FIG. 2 but with the membrane-tipped pipette 110 shown in FIG. 10 replaced by a magnetic member 110' similar to that in FIG. 17. Reagents and volumes are given in Table 5. Sample (15 μL) was allowed to react with the Reagent Formulation (5 μL) of the seventh well 42, containing anti-BNP antibody 1 conjugated to 0.5

µm paramagnetic particles (1.25%) and 0.2 µm latex particles coated with HRP and anti-BNP antibody 2 (0.3%). Formation Anti-BNP 1-BNP-anti BNP 2/HRP complex was allowed to proceed for 10 minutes at ambient temperature, then wash buffer (165 µL) was added and the magnetic member was introduced into the diluted reaction mixture.

The paramagnetic particles of the Reagent Formulation, including bound BNP/anti-BNP2/HRP, were attracted to the magnetic member. The magnetic member, with bound BNP/anti-BNP2/HRP, was removed, while unbound anti-BNP 2/HRP remained in the well. The magnetic member was washed extensively in the third, fourth and eighth wells 34, 36, 44. Finally the magnetic member was immersed in the TMB solution of the fifth well 38 and the absorption increase monitored for 750 s at 625 nm. FIG. 23 shows the dose-response graph. The achieved Limit of Detection was 18 pg/mL.

TABLE 5

Reagents and volumes of BNP assay

| Well nr. | Content | Volume |
|---|---|---|
| | Base member | |
| 3rd | Wash buffer | 300 µL |
| 4th | Wash buffer | 300 µL |
| 5th | TMB solution | 200 µL |
| | Extension member | |
| 6th | Wash buffer | 400 µL |
| 7th | Reagent formulation | 5 µL |
| 8th | Wash buffer | 300 µL |

EXAMPLE 8

Five different magnets were tested with respect to capture of paramagnetic microspheres and generation of colour, using the set-up and protocol described in Example 7 and a sample containing 400 pg/mL BNP. Results are depicted in Table 6. The size and shape of the magnet was found to affect the efficiency of paramagnetic microsphere capture and assay performance. The best performance was achieved using a magnet with a perfect fit to the sleeve cavity of the magnetic member (15×3.2×1.3), similar to the arrangement shown in FIG. 17.

TABLE 6

| Shape | Size (mm) | No. | Capture of MP (%) | Absorbance (mAU at 625 nm) |
|---|---|---|---|---|
| disc | 2.0 × 1.3 | 1 | 54 ± 4 | 332 ± 63 |
| | | 2 | 56 ± 13 | 414 ± 100 |
| trapezoid prism | 7.2 × 1.6 × 1.3 | 1 | 68 ± 17 | 480 ± 141 |
| | 10 × 1.6 × 1.3 | 1 | 89 ± 4 | 512 ± 40 |
| | 15 × 3.2 × 1.3 | 1 | 98 ± 2 | 569 ± 91 |

In summary, preferred embodiments of the invention provide a novel assay cartridge which enables a wide range of assays to be conveniently and usefully performed.

The invention claimed is:

1. A cutter for an assay cartridge comprising a base member defining two or more wells and a cap member configured to carry a pipette positionable in at least two of said wells, wherein the cutter is positioned on an inside surface of said cap member, and wherein said cutter comprises first and second blades for shearing a foil seal covering one of the wells and a third blade extending between the first and second blades, spaced away from an end of the first and second blades, the first and second blades being linear and parallel to each other, wherein said first and second blades slope downward from each end away from the inside surface of the cap member to their respective midpoints, wherein the midpoints of the first and second blades point toward the foil seal when the cutter is urged toward the foil seal, and wherein said third blade slopes downward from its midpoint away from the inside surface of the cap member toward the midpoints of said first and second blades such that the first and second blades shear said foil seal adjacent respective walls of said well from a midpoint of said foil seal outwards and wherein said third blade shears said foil seal along a line between said walls.

2. An assay cartridge comprising a base member defining two or more wells and a cap member configured to carry a pipette positionable in at least two of said wells, and further comprising a cutter as claimed in claim 1 located in the cap member.

3. The cutter of claim 1, wherein said third blade is configured to cut said foil seal perpendicular to said first and second blades.

4. The cutter of claim 1, wherein said cutter is rectangular in outline and comprises short edges of said rectangle and long edges of said rectangle.

5. The cutter of claim 4, wherein said first and second blades are situated along said short edges of said rectangle.

6. The cutter of claim 4, wherein said third blade is situated between and perpendicular to said first and second blades.

7. The cutter of claim 1, wherein said third blade comprises a pair of cutting edges that slope downward from the midpoint of the third blade away from the inside surface of the cap member to meet said first and second blades.

8. The cutter of claim 7, wherein said cutting edges of said third blade meet said first and second blades at the midpoint of said first and second blades.

9. The cutter of claim 1, wherein said cap member further comprises a plurality of ridges located along an edge of said cutter that are configured to push flaps of cut foil against inside edges of said wells.

* * * * *